United States Patent
Pullen

(10) Patent No.: US 8,236,336 B2
(45) Date of Patent: Aug. 7, 2012

(54) ADJUVANT COMPOSITION FOR USE WITH HERBICIDES, PESTICIDES, INSECTICIDES, OVICIDES AND FUNGICIDES AND METHOD OF APPLICATION

(75) Inventor: Erroll M. Pullen, Bantry Bay (ZA)

(73) Assignee: Oro Agri, Inc., Trophy Club, TX (US)

(*) Notice: Subject to any disclaimer, the term of this patent is extended or adjusted under 35 U.S.C. 154(b) by 1211 days.

(21) Appl. No.: 11/984,029

(22) Filed: Nov. 13, 2007

(65) Prior Publication Data

US 2008/0070787 A1  Mar. 20, 2008

Related U.S. Application Data

(63) Continuation of application No. 10/641,823, filed on Aug. 16, 2003, now Pat. No. 7,341,735, which is a continuation-in-part of application No. 10/188,025, filed on Jul. 1, 2002, now Pat. No. 7,294,341.

(60) Provisional application No. 60/344,671, filed on Dec. 31, 2001.

(51) Int. Cl.
| A01N 25/00 | (2006.01) |
| A01N 25/24 | (2006.01) |
| A01N 25/32 | (2006.01) |
| A01N 37/18 | (2006.01) |
| A01N 59/00 | (2006.01) |
| A01N 61/00 | (2006.01) |

(52) U.S. Cl. ............ 424/405; 424/406; 424/407; 514/1; 514/4.5; 514/974

(58) Field of Classification Search .................. None
See application file for complete search history.

(56) References Cited

U.S. PATENT DOCUMENTS

| 3,584,119 A | 6/1971 | Langley |
| 4,039,588 A | 8/1977 | Wilson et al. |
| 4,379,168 A | 4/1983 | Dotolo |
| 4,610,881 A | 9/1986 | Bechgaard |
| 5,087,353 A | 2/1992 | Todd et al. |
| 5,110,804 A | 5/1992 | Lee |
| 5,118,506 A | 6/1992 | Eichoefer |
| 5,143,939 A | 9/1992 | Browning |
| 5,330,671 A | 7/1994 | Pullen et al. |
| 5,374,600 A | 12/1994 | Hozumi et al. |
| 5,389,257 A | 2/1995 | Todd et al. |
| 5,444,078 A | 8/1995 | Yu et al. |
| 5,527,482 A | 6/1996 | Pullen et al. |
| 5,641,847 A | 6/1997 | Hozumi et al. |
| 5,693,344 A | 12/1997 | Knight et al. |
| 5,744,137 A | 4/1998 | Stone |
| 5,753,593 A | 5/1998 | Pullen et al. |
| 5,863,456 A | 1/1999 | Pullen |
| 5,871,765 A | 2/1999 | Johnson et al. |
| 5,876,622 A | 3/1999 | Pullen et al. |
| 5,885,600 A | 3/1999 | Blum et al. |
| 5,900,243 A | 5/1999 | Yoder et al. |
| 5,948,743 A * | 9/1999 | Fonsny et al. ............... 510/280 |
| 5,958,287 A | 9/1999 | Pullen |
| 5,977,186 A | 11/1999 | Franklin |
| 6,093,856 A | 7/2000 | Cripe et al. |
| 6,124,366 A | 9/2000 | Pullen et al. |
| 6,130,253 A | 10/2000 | Franklin et al. |
| 6,248,710 B1 | 6/2001 | Bijsterbosch et al. |
| 6,251,951 B1 | 6/2001 | Emerson et al. |
| 6,258,369 B1 | 7/2001 | Pullen |
| 6,277,389 B1 | 8/2001 | Pullen |
| 6,455,086 B1 | 9/2002 | Trinh et al. |
| 6,500,445 B1 | 12/2002 | Pullen |
| 6,514,512 B1 * | 2/2003 | Puterka et al. ............... 424/421 |
| 6,582,712 B2 | 6/2003 | Pullen |
| 6,689,342 B1 * | 2/2004 | Pan et al. ..................... 424/49 |
| 7,294,341 B2 * | 11/2007 | Pullen ......................... 424/405 |
| 7,341,735 B2 * | 3/2008 | Pullen ......................... 424/405 |
| 2003/0060379 A1 * | 3/2003 | Souter et al. ................. 510/131 |
| 2003/0224939 A1 | 12/2003 | Miles |
| 2004/0138176 A1 | 7/2004 | Miles et al. |
| 2008/0064603 A1 | 3/2008 | Pullen |
| 2008/0214400 A1 | 9/2008 | Pullen |
| 2010/0144534 A1 | 6/2010 | Pullen |

FOREIGN PATENT DOCUMENTS

| EP | 0943239 | 9/1990 |
| WO | 97/16975 | 5/1997 |
| WO | 98/02044 | 1/1998 |
| WO | 01/13726 | 3/2001 |
| WO | WO0126457 | * 4/2001 |
| WO | 03/020024 | 3/2003 |
| WO | 03/056917 | 7/2003 |
| WO | 2006/052228 | 5/2006 |
| WO | 2008/097553 | 8/2008 |
| WO | 2011/031287 | 3/2011 |

OTHER PUBLICATIONS

Tripathi N. N. et al., "Toxicity of Some Terpenoids Against Fungi Infesting Fruits and Seeds of Capsicum-Annuum During Storate", Phytopatologische Zeitschrift, 1984, pp. 328-335, vol. 110, Verlag Paul Parey, Berlin, DE.

* cited by examiner

Primary Examiner — Debbie K Ware
(74) Attorney, Agent, or Firm — Milbank, Tweed, Hadley & McCloy LLP

(57) ABSTRACT

An adjuvant for use with systemic herbicides, pesticides, insecticides, ovicides and fungicides and method of application on animals, birds, trees, plants, fruits and vegetables to enhance the action and effect of systemic herbicides, pesticides, insecticides, ovicides and fungicides with which the adjuvant is combined wherein the adjuvant comprises at least one surfactant and at least one high terpene containing natural oil.

15 Claims, No Drawings

ADJUVANT COMPOSITION FOR USE WITH HERBICIDES, PESTICIDES, INSECTICIDES, OVICIDES AND FUNGICIDES AND METHOD OF APPLICATION

CROSS REFERENCE

This application claims priority to and is a continuation of U.S. patent application Ser. No. 10/641,823 filed Aug. 16, 2003 now U.S. Pat. No. 7,341,735, which is a continuation-in-part of application Ser. No. 10/188,025 filed Jul. 1, 2002 now U.S. Pat. No. 7,294,341, which claims priority to provisional application Ser. No. 60/344,671 filed Dec. 31, 2001, the disclosures of which are hereby incorporated by reference in their entireties.

BACKGROUND OF THE INVENTION

1. Field of the Invention

An adjuvant for use with systemic herbicides, pesticides, insecticides, ovicides and fungicide on animals, birds, plants, trees, fruits and vegetables.

2. Description of the Prior Art

Various insects such as lice, ticks, mites and aphides attack untreated and unprotected trees and plants. Moreover, fungi left uncontrolled can damage and even destroy plants and trees including crops associated therewith.

In the past, various oils have been used to control insects and mites. Recently, however, renewed attention has focused on the use of oils as a natural substitute for traditional insecticides with attendant toxic and other dangerous side effects.

These oils include horticultural oils that are highly refined petroleum products than can be mixed with water for application for control of target insect and mite pests without deleterious effects. Modern horticultural oils do not include vegetable, fish or whale oils.

Horticultural spray oils are the low toxicity alternative to broad-spectrum insecticides. Since the mechanism of insect and mite control with spray oils is by suffocation and/or repellency of egg laying females, there is no requirement for the addition of toxic chemicals. These properties are a valuable and well-recognized component of the practice of integrated pest management where oil spraying is intrinsically linked to natural control of pests by predators and parasitoids. Horticultural spray oils are formulated on highly refined clear oil with a minimum of nonionic surfactant. Independent environmental impact studies have shown that D-C-TRON has no detrimental effect on the environment. Mammalian toxicity studies published in the American Journal of Industrial Medicine have shown that oils at this refinement level are non-toxic and non-carcinogenic.

Generally, oil sprays are safe to humans. These oil sprays have little, if any, negative effect on wildlife and non-target insects in the environment. Furthermore, oil sprays are less toxic due to the method by which they kill target pests. In particular, the thin film of oil covers the target insect or mite and plugs the spiracles or pores through which the pests or parasites breathe. The cause of death is primarily suffocation. Large, motile insects and animals that breathe by another method are not affected by these oils.

Another advantage of oil applications is the absence of objectionable odors. In addition, oils are relatively inexpensive and significantly less expensive than many insecticides.

Unfortunately, there are limitations to the use of oil treatments. For example, oils are only effective against those pests that are thoroughly coated by the spray solution. This usually means that only small, immobile or slow moving pests that are exposed on the surface of the plant or tree at the time of application will be controlled.

Since oil sprays only work by contracting and covering the target pest, thorough application is essential. Missed surface areas provide a safe refuge for the target pests.

U.S. Pat. No. 6,258,369 and U.S. Pat. No. 6,277,389 disclose a non-toxic aqueous pesticide for application on plants and animals comprising at least one surfactant and at least one high terpene containing natural oil. The pesticide is used to effectively control insects and parasites such as darkling beetles, lice, ticks, mites, flies, aphides, mosquitoes and chiggers found on plants and animals.

U.S. Pat. No. 5,693,344 shows a hazard-free method for controlling insects using a non-toxic composition in the form of a fragrance and crystalline particles which puncture directly through the exoskeleton of an insect. In operation, the particles work themselves between the insect's protective body plates and then puncture the exoskeleton permitting entry of the fragrance into the body of the insect. Once inside, the particles absorb up to four times their weight of the vital body fluids of the insect and the fragrance has a neural effect on the insect.

U.S. Pat. No. 5,143,939 shows a method of treating soil and agricultural crops for controlling worms and nematodes comprising a nonionic surfactant, namely an alkylox-ypolyethyl-eneoxyethanol used as the sole active ingredient to control fungus, mites, worms, termites, nematodes and other insects.

U.S. Pat. No. 4,379,168 relates to pesticides containing d-limonene as an insect-killing ingredient with surfactants or emulsifiers and water. The pesticide compositions are liquids designed for use as a dip to rid small animals of fleas and ticks, a spray to kill fleas and ticks on small animals and in the kennels of small animals; a spray to kill flies on small animals and in the kennels of small animals; and a spray or liquid to rid household areas of cockroaches and other insect pests.

U.S. Pat. No. 6,248,710 B1 discloses a water-soluble or water-dispersible material for deposition onto a fabric substrate during a treatment process comprising polysaccharide structure having at least one substituent benefit agent group and optionally, one or more other substituent groups. The polysaccharide structure has one or more regions with at least 3, preferably at least 4 consecutive unsubstituted saccharide rings.

SUMMARY OF THE INVENTION

The present invention relates to an adjuvant formulated for use on animals, birds, plants, trees, fruits and vegetables as an adjuvant in combination with systemic herbicides, pesticides, insecticides, ovicides and fungicide. The composition comprises at least one surfactant and at least one high terpene. The invention also includes the method of application of the composition.

High terpene containing natural oil as used herein means those natural oils having a terpene content of at least 50 per cent. It is preferable that the high terpene natural oil contains at least 65 per cent. Suitable high terpene containing natural oils includes oil from conifers such as citrus peel oils, preferably orange oil, grapefruit oil, lemon oil or pine oil. Of these, orange oil is preferred and cold pressed orange oil the most preferred. The preferred terpene content is from about 80 per cent to about 90 per cent and most preferred from about 85 per cent to about 87 per cent, all by weight.

The amount of high terpene containing natural oils in the composition depends upon the amount of terpenes in the specific oil used. Generally, the composition contains from about 2 per cent by weight to about 8 per cent by weight of high terpene containing natural oil, preferably about 5 per cent by weight.

Anionic and nonionic surfactants are acceptable for use in the composition of the present invention. Anionic surfactants such as salts of fatty acids, alkyl sulphates, alkyl ether sulphonates and alkyl aryl sulphonates are preferred.

The composition may also contain preservatives, pH neutralizers and/or clarifiers or stabilizers. The balance of the composition is water.

In use, the adjuvant, when combined with systemic herbicides, pesticides, insecticides, ovicides and fungicides, is diluted and sprayed or misted on animals, birds, plants, trees, fruits or vegetables.

When so applied, the composition is effective as an adjuvant in enhancing the effect of systemic herbicides, insecticides, ovicides and fungicides that are applied to control various diseases, pests and insects including darkling beetles, lice, ticks, mites, flies, aphids, thrips, mealybugs, mosquitoes and chiggers.

The composition is also effective as an adjuvant in enhancing fungicides in controlling fungi. While not to be bound by theory, absorption of fungicide, once blended with the adjuvant, is increased both in speed as well as percentage absorbed.

Finally, the composition as an adjuvant enhances water penetration and absorption by the soil as well as decreases water logging. These better soil conditions lead to improved root and plant growth.

The invention accordingly comprises the features of construction, combination of elements, and arrangement of parts that will be exemplified in the construction hereinafter set forth, and the scope of the invention will be indicated in the claims.

DETAILED DESCRIPTION OF THE PREFERRED EMBODIMENT

The present invention relates to an adjuvant for use with systemic herbicides, pesticides, insecticides, ovicides and fungicides formulated for use with various animals, birds, trees, plants, fruits and vegetables. The composition comprises at least one surfactant and at least one high terpene containing oil to enhance the effectiveness of pesticides, insecticides, ovicides and fungicides in controlling pests, insects and fungi. The invention also includes the method of application of the composition. Furthermore, the composition may be used as an adjuvant with contact pesticides.

High terpene containing natural oil as used herein means those natural oils having a terpene content of at least about 50 per cent. It is preferable that the high terpene natural oil contains at least about 65 per cent. Suitable high terpene containing natural oils includes oil from conifers such as citrus peel oils, preferably orange oil, grapefruit oil, lemon oil or pine oil. Of these, orange oil is preferred and cold pressed orange oil the most preferred. The preferred terpene content is from about 80 per cent to about 90 per cent and most preferred from about 85 per cent to about 87 per cent, all by weight.

The amount of high terpene containing natural oils in the composition depends upon the amount of terpenes in the specific oil used. Generally, the composition contains from about 2 per cent by weight to about 8 per cent by weight of high terpene containing natural oil, preferably about 5 per cent by weight.

Anionic and nonionic surfactants are acceptable for use in the composition of the present invention. Anionic surfactants such as salts of fatty acids, alkyl sulphates, alkyl ether sulphonates and alkyl aryl sulphonates are preferred. Examples of such surfactants may include from about 8 per cent to about 12 per cent sulfonic acid, preferably about 10 per cent sulfonic acid; from about 5 per cent to about 9 per cent sodium laurel sulfate, preferably about 6.8 per cent sodium laurel sulfate; from about 6 per cent to about 10 per cent alcohol ethoxylate, preferably about 8.2 per cent alcohol ethoxylate; and from about 1 per cent to about 3 per cent olefin sulfonate, preferably about 1.7 olefin sulfonate, all by weight.

Generally, the composition contains from about 20 per cent to about 34 per cent surfactant(s), preferably from about 25 per cent to about 30 per cent surfactant(s) and most preferably about 26.7 per cent surfactant(s), all by weight.

The composition may also include butylated hydroxytoluene, p-Hydroxybenzoic acid and/or sodium tetraborate decahydrate. The range of butylated hydroxytoluene is from about 0.05 per cent to about 0.15 per cent and preferably about 0.10 per cent, all by weight. The range of sodium tetraborate decahydrate is from about 0.89 per cent to about 1.09 per cent and preferably about 0.99 per cent, all by weight. The range of p-Hydroxybenzoic acid is from about 0.25 per cent to about 0.35 per cent and preferably about 0.30 per cent, all by weight. Generally, the composition contains from about 1.39 per cent to about 1.89 per cent preservative(s), preferably about 1.64 per cent preservative(s), all by weight.

In addition, a bactericide is from about 0.05 per cent to about 0.15 per cent and preferably about 0.10 per cent, all by weight may be added.

Caustic crystals such as sodium hydroxide may be added in an amount of from about 1.25 per cent to about 1.37 per cent by weight to neutralize the composition to a pH of from about 7.75 to about 9.

A clarifier or stabilizer such as urea may be added in an amount of from about 0.59 per cent to about 0.99 per cent and preferably about 0.79 per cent, all by weight.

The balance of the composition is made up by water.

The preferred composition comprises about 5 per cent cold pressed orange oil, about 6.8 per cent sodium lauryl sulfate, about 8.2 per cent of alcohol ethoxylate, about 1.7 per cent sodium olefin sulfonate, about 10 per cent dodecylbenzene sulphonic acid, about 0.1 per cent antioxidant such as butylate hydroxytoluene, about 0.30 per cent preservative such as p-Hydroxybenzoic acid, about 0.1 per cent bactericide, about 0.99 per cent fungicide such as sodium tetraborate decahydrate, about 0.79 per cent clarifier such as urea and about 1.31 per cent neutralizer such as sodium hydroxide with the balance a diluent such as water, all by weight.

In use, the adjuvant composition is combined with a herbicide, pesticide, insecticide, ovicide or fungicide effective as either a contact or systemic herbicide, pesticide, insecticide, ovicide or fungicide. An effective range for the adjuvant composition is from about ½ part to about 8 parts adjuvant to 1000 parts herbicide, pesticide, insecticide, ovicide or fungicide and water. The preferred range for the adjuvant composition is from about 1½ parts to about 4 parts adjuvant composition to 1000 parts herbicide, pesticide, insecticide, ovicide, fungicide. The preferred concentration of adjuvant concentration is about 2 parts adjuvant composition to 1000 parts herbicide, pesticide, insecticide, ovicide or fungicide.

The combined adjuvant composition and herbicide, pesticide, insecticide, ovicide or fungicide is applied to plants or row crops such as most vegetables at an application rate of about five (5) liters or less per acre.

The combined adjuvant composition and herbicide, pesticide, insecticide, ovicide or fungicide is applied to trees or orchards at an application rate of about eight (8) liters or less per acre.

While the invention has been described above with respect to certain particular embodiments thereof, numerous other forms and modifications will be apparent to those skilled in the art. The appended claims and the invention generally should be construed as covering all such obvious forms and modifications that are within the true spirit and scope of the invention.

It will thus be seen that the objects set forth above, among those made apparent from the preceding description are efficiently attained and since certain changes may be made in the above construction without departing from the scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

Now that the invention has been described,

What is claimed is:

1. A composition consisting of:
   a) from 0.001% to 0.064% by weight orange oil;
   b) from 0.01% to 0.27% by weight surfactant;
   c) an agent selected from the group consisting of a herbicide, an ovicide, a fungicide, and a pesticide; and
   d) water.

2. The composition of claim 1, wherein said orange oil is present in an amount from 0.001% to 0.016% by weight orange oil.

3. The composition of claim 1, wherein said orange oil is present in an amount from 0.004% to 0.016% by weight orange oil.

4. The composition of claim 1, wherein said orange oil is present in an amount from 0.004% to 0.064% by weight orange oil.

5. The composition of claim 1, wherein said surfactant is present in an amount from 0.004% to 0.017% by weight surfactant.

6. The composition of claim 1, wherein said surfactant is present in an amount from 0.16% to 0.27% by weight surfactant.

7. The composition of claim 1, wherein said agent is an herbicide.

8. The composition of claim 1, wherein said agent is an ovicide.

9. The composition of claim 1, wherein said agent is a fungicide.

10. The composition of claim 1, wherein said agent is a pesticide.

11. The composition of claim 10, wherein said pesticide is a miticide.

12. The composition of claim 10, wherein said pesticide is an insecticide.

13. The composition of claim 1, wherein said surfactant is selected from the group consisting of sulfonic acid, sodium laurel sulfate, alcohol ethoxylate and olefin sulfonate.

14. Treated trees or treated orchards comprising the composition of claim 1.

15. Treated plants vegetables or treated row crops comprising the composition of claim 1.

* * * * *